United States Patent [19]
Bandman et al.

[11] Patent Number: 6,090,377
[45] Date of Patent: Jul. 18, 2000

[54] MONOCYTE ACTIVATING CYTOKINE

[75] Inventors: Olga Bandman; Roger Coleman, both of Mountain View; Janice Au-Young, Berkeley; Lynn E. Murry, Portola Valley, all of Calif.

[73] Assignee: Incyte Pharmaceuticals, Inc., Palo Alto, Calif.

[21] Appl. No.: 09/123,615

[22] Filed: Jul. 28, 1998

Related U.S. Application Data

[62] Division of application No. 08/705,868, Aug. 28, 1996.

[51] Int. Cl.[7] .......................... C12N 15/19; C07K 14/52; A61K 38/19
[52] U.S. Cl. ...................... 424/85.1; 530/351; 435/69.5; 435/71.2; 435/471; 435/325; 435/252.3; 435/320.1; 536/23.5
[58] Field of Search .......................... 530/351; 435/69.5, 435/71.1, 71.2, 471, 325, 252.3, 320.1; 536/23.1, 23.5; 424/85.1

[56] References Cited

FOREIGN PATENT DOCUMENTS

95/09180  4/1995  WIPO.
96/40719  12/1996  WIPO.
97/10841  3/1997  WIPO.

OTHER PUBLICATIONS

Kao, et al., "Characterization of a Novel Tumor-derived Cytokine," *J. Biol. Chem.*, vol. 269(40), pp. 25106–25119, 1994.

Ribas de Pouplana et al., "Evidence that two present-day components needed for the genetic code appeared after nucleated cells separated from eubacteria," *Proc. Nat'l. Acad. Sci. USA*, vol. 93, pp. 166–170, 1996.

Kao et al., "A Peptide Derived from the Amino Terminus of Endothelial–Monocyte-activating Polypeptide . . . ," *J. Biol. Chem.*, vol. 269(13), pp. 9774–9782, 1994.

*Primary Examiner*—Prema Mertz
*Attorney, Agent, or Firm*—Leanne C. Price; Incyte Pharmaceuticals, Inc.

[57] ABSTRACT

The present invention provides novel monocyte activating cytokine (MAC) and a polynucleotide encoding MAC. The invention also provides for genetically engineered expression vectors and host cells comprising the nucleic acid sequence encoding MAC. The invention also provides for the production and use of substantially purified MAC in pharmaceutical compositions for the treatment of cancer and disease of the immune system. The invention also describes diagnostic assays which utilize the polynucleotide to hybridize with the transcripts encoding MAC and antibodies which specifically bind to MAC.

2 Claims, 10 Drawing Sheets

```
                                9          18        27        36        45        54
          5'  GG CCC GCT GCG CTG AGA CAC TGA AGG GGT GTC CGG GAG CTG AAA GCG TGT
                      63        72        81        90        99       108
              AGA CCT CGC GAC GGT CCC GCG GTA GAC ATC GAT ATA AGA AGT AAT GGG CTG CCA
                     117       126       135       144       153       162
              CAG AGC CCA AAT TCC CTG CTG TTC GAC TGG CTT TGC AGA ATT TTG ACA TGA CTT
                     171       180       189       198       207       216
              ACA GTG TGC AGT TTG GAG ATC TTT GGC CAT CAA TCC GTG TCA GTC TCC TCT CAG
                     225       234       243       252       261       270
              AGC AGA AGT ATG GTG CAC TGG TCA ATA ACT TTG CTG CCT GGG ATC ATG TAA GTG
                     279       288       297       306       315       324
              CTA TGG AGC AGC TGA GTG CCA AGG ATT TTG TGA ATG AAG CCA TCT CCC ACT
                                                          M   K   P   S   P   T
                     333       342       351       360       369       378
              GGG AAC TGC AGT CTG AGG GTG GCC AAT CTG CAG CCC CAT CCC CTG CCT CCT GGG
               G   N   C   S   L   R   V   A   N   L   Q   P   H   P   L   P   P   G
```

FIGURE 1A

```
    387        396        405        414    423        432
CCT GCA GTC CGA ACC TTC GAT GCT TCA CTT TTG ACA GAA GGG ATA ACA GTC GCT
 P   A   V   R   T   F   D   A   S   L   L   T   E   G   I   T   V   A 441        450        459        468    477        486
TCC CTC CTG CCA GAG TTT GTG ATC CTA CGA GAT GAG AAA TGG GGA AAC AAA
 S   L   L   P   E   F   V   I   L   R   D   E   K   W   G   N   K 495        504        513        522    531        540
ACC TAC ACA GCT TAC GTG GAC CTG GAA AAG GAC TTT GCT GCT GAA GTT GTA CAT
 T   Y   T   A   Y   V   D   L   E   K   D   F   A   A   E   V   V   H 549        558        567        576    585        594
CCT GGA GAC CTG AAG AAT TCT GTT GAA GTC GCA CTG AAC AAG TTG CTG GAT CCA
 P   G   D   L   K   N   S   V   E   V   A   L   N   K   L   L   D   P 603        612        621        630    639        648
ATC CGG GAA AAG TTT AAT ACC CCT GCC CTG AAA AAA CTG GCC AGC GCT GCC TAC
 I   R   E   K   F   N   T   P   A   L   K   K   L   A   S   A   A   Y 657        666        675        684    693        702
CCA GAT CCC TCA AAG CAG AAG CCA ATG GCC AAA GGC CCT GCC AAG AAT TCA GAA
 P   D   P   S   K   Q   K   P   M   A   K   G   P   A   K   N   S   E 711        720        729        738    747        756
CCA GAG GAG GTC ATC CCA TCC CGG CTG GAT ATC CGT GTG GGG AAA ATC ATC ACT
 P   E   E   V   I   P   S   R   L   D   I   R   V   G   K   I   I   T
```

FIGURE 1B

```
                765              774              783              792              801              810
GTG GAG AAG CAC CCA GAT GCA GAT GCA AGC CTG TAT GTA GAG AAG ATT GAC GTG GGG
 V   E   K   H   P   D   A   D   A   S   L   Y   V   E   K   I   D   V   G 819              828              837              846              855              864
GAA GCT GAA CCA CGG ACT GTG GTG AGC GGC CTC GTA CAG TTC GTG CCC AAG GAG
 E   A   E   P   R   T   V   V   S   G   L   V   Q   F   V   P   K   E 873              882              891              900              909              918
GAA CTG CAG GAC AGG CTG GTA GTG CTG TGC AAC CTG AAA CCC CAG AAG ATG
 E   L   Q   D   R   L   V   V   L   C   N   L   K   P   Q   K   M 927              936              945              954              963              972
AGA GGA GTC GAG TCC CAA GGC ATG CTT CTG TGT GCT TCT ATA GAA GGG ATA AAC
 R   G   V   E   S   Q   G   M   L   L   C   A   S   I   E   G   I   N 981              990              999             1008             1017             1026
CGC CAG GTT GAA CCT CTG GAC CCT CCG GCA GGC TCT GCT CCT GGT GAG CAC GTG
 R   Q   V   E   P   L   D   P   P   A   G   S   A   P   G   E   H   V 1035             1044             1053             1062             1071             1080
TTT GTG AAG GGC TAT GAA AAG GGC CAA CCA GAT GAG GAG CTC AAG CCC AAG AAG
 F   V   K   G   Y   E   K   G   Q   P   D   E   E   L   K   P   K   K 1089             1098             1107             1116             1125             1134
AAA GTC TTC GAG AAG TTG CAG GCT GAC TTC AAA ATT TCT GAG GAG TGC ATC GCA
 K   V   F   E   K   L   Q   A   D   F   K   I   S   E   E   C   I   A
```

FIGURE 1C

```
     1143                1152            1161            1170            1179         1188
CAG TGG AAG CAA ACC AAC TTC ATG ACC AAG CTG GGC TCC ATT TCC TGT AAA TCG
 Q   W   K   Q   T   N   F   M   T   K   L   G   S   I   S   C   K   S 1197                1206            1215            1224            1233         1242
CTG AAA GGG GGG AAC ATT AGC TAG CCA GCC CAG CAT CTT CCC CCC TTC TTC CAC
 L   K   G   G   N   I   S 1251                1260            1269            1278            1287         1296
CAC TGA GTC ATC TGC TGT CTC TTC AGT CTG CTC CAT CCA TCA CCC ATT TAC CCA 1305                1314            1323            1332            1341         1350
TCT CTC AGG ACA CGG AAG CAG CGG GTT TGG ACT CTT TAT TCG GTG CAG AAC TCG 1359                1368            1377            1386            1395         1404
GCA AGG GGC AGC TTA CCC TCC CCA GAA CCC AGG GAT CAT CCT GTC TGG CTG CAG 1413                1422            1431            1440            1449
TGA GAG ACC AAC CCC TAA CAA GGG CTG GGC CAC AGC AGG GAG TCC A 3'
```

FIGURE 1D

```
  1   MKPSPTGNCSLR-VANLQPHPLPPGPAVRTF--D-------                    627856
  1   M---ATNDAVLK--REQKGAEADQIIEYLKQQ----                       g 498910
  1   MGDAPSPEEKLHLITRNLQEVLGEEKLKEIHLKERELKIYW                  g 1184699

32   --------------------ASLLT---EGITVASLLPEFV                    627856
 29   --------------------VALLK---EKAILQATMREEK                 g 498910
 41   GTATTGKPHVAYFVPMSKIADFLKAGCEVTILFADLHAYL                  g 1184699

50   ILRDEKWGGNKTYTAYVDLEKDFAAEVVHPG---DLKNSVE                    627856
 47   KLRVEN---AKLKKEIEELKQELILAEIHNGVEQVRVRLS                  g 498910
 81   DNMKAPWELLELRVSYYENVIKAMLESIGVPLEKLKFIKG                  g 1184699

88   VA---LNK-------------LLDPIREKFNTPALKKLASAA                   627856
 84   TP---LQTNCTAS-----ESVVQSPSVATTASPATKEQIKAG                g 498910
121   TDYQLSKEYTLDVYRLSSVVTQHDSKKAGAEVVKQVEHPL                  g 1184699

114   YPDPSKQKPMAKGPAKN-------SEPEEEVI--PSRLDI                     627856
118   EEKKVKEKTEKKGEKKEKQQSAAASTDSKPHID--ASRLDL                 g 498910
161   LSGLLYPGLQALDEEYLKGEYLKEYLKDAQFGGIDQRKIFTFAEKYLP          g 1184699

144   RVGKIITVE--KHPDADSLYVEKIDVGEAEPRTVVSGLVQF                    627856
156   RIGCIVTAK--KHPDADSLYVEEVDVGEAAPRTVVSGLVNH                 g 498910
201   ALGYSKRVHLMNPMVPGLTGSKMSSSEEESKI--DLLD-                   g 1184699
```

```
          10        20        30        40        50        60        70
MKPSPTGNCSLRVANLQPHPLPPGPAVRTFDASLLTEGITVASLLPEFVILRDEKWGGNKTYTAYVDLEK
HELIX          hhhhhhh              hhhhhhhhh          hhhhhhhhh        hhhhHHH
SHEET    sSSSSSSs          SSSSSSSSSsSSSSSSSSSSSSSs               ssSSSSSs
TURN  TTTTTTTT      TTTTTTTTT                                TTTTTT
COIL           C                                       C 80        90        100       110       120       130       140
DFAAEVVHPGDLKNSVEVALNKLLDPIREKFNTPALKKLASAAYPDPSKQKPMAKGPAKNSEPEEVIPSR
HELIX HHHHHHHh        hhHHHHHHHHH         HHHHHHHHH                   hhHHHHh
SHEET           sssssssssSSS
TURN                                                       TTTTTT         TTTT
COIL                                CCCCCCC                     CCC 150       160       170       180       190       200       210
LDIRVGKIITVEKHPDADSLYVEKIDVGEAEPRTVVSGLVQFVPKEELQDRLVVLCNLKPQKMRGVESQ
HELIX         hhHHHHh            hhHHHHHHHhhhhh       HHHHHhhhhHHHHHHHHHh
SHEET sSSSSSSSSs                        ssssss                  SSSSSSSSSs          s
TURN  T         TTTTTTT      TTTT TTTT                                        TT
COIL
```

FIGURE 5A

```
       220         230         240         250         260         270         280
GMLLCASIEGINRQVEPLDPPAGSAPGEHVFVKGYEKGQPDEELKPKKKVFEKLQADFKISEECIAQWKQ
HELIX hhhhhH                   hhhhHhhhhH      hhhhHHh     hHHHHHHHHHHhhhhhh
SHEET ssSSSSSS    SSSSSSS              SSSsSS              ssssssss       SSSSSSS
TURN  TT              TTTTTTTTT              TTTT TTTTT
COIL            CC                           CCC
      TNFMTKLGSISCKSLKGGNIS*
HELIX hhhhH
SHEET SSSsSSS
TURN         TTTTTTTT
COIL    CCCC         C
        290        300
```

FIGURE 5B

MONOCYTE ACTIVATING CYTOKINE

This application is a divisional application of U.S. application Ser. No. 08/705,868, filed Aug. 28, 1996.

FIELD OF THE INVENTION

The present invention relates to nucleic acid and amino acid sequences of a novel monocyte activating cytokine which shares features with other proteins involved in cell proliferation, differentiation, and chemotaxis and to the use of these sequences in the diagnosis, study, prevention and treatment of disease.

BACKGROUND OF THE INVENTION

Cytokines are active in cell proliferation, differentiation and movement. At picomolar to nanomolar concentrations, they effect such activities as leukocyte migration and function, hematopoietic cell numbers, temperature regulation, acute response to infections, tissue remodeling, and cell survival. Since cytokines are produced in groups and in patterns characteristic of a particular stimulus or disease, studies using antibodies or other drugs to modify the activity of a particular cytokine are beginning to elucidate the roles of individual cytokines in pathology and physiology.

Endothelial-monocyte activating polypeptide II (EMAP-II) was first identified by Kao J et al (1994 J Biol Chem 269:25106–25119) in the supernatant of murine methylcholanthrene A-induced fibrosarcomas (METH A), where EMAP-II functions to activate host cells. The full length cDNA which Kao et al cloned has 1086 bp and three ATG codons. Using Kozak's rules, Kao et al selected the second ATG, at position 64, as the most probable start codon and predicted that translation would produce a polypeptide of 310 amino acids and 34 kDa.

The mature EMAP-II is a unique, leaderless, single chain polypeptide with a predicted molecular mass of 20 kDa which most likely results from processing of the larger polypeptide. Using a fragment of the murine cDNA as a probe, Kao et al identified a human cDNA from a monocyte library with 86% identity. Both the designated start codon and the upstream ATG are conserved in the human cDNA.

The processing of the mature murine and human EMAP-II proteins appears to be conserved and shared among several other processed cytokines including interleukin-8 (IL-8), IL-1β, and in von Willebrand antigen II. IL-1β, which is approximately the same size as EMAP-II, also lacks a classic signal peptide and must be cleaved by the cysteine protease IL-1β-converting enzyme at a conserved aspartate residue in the P-1 position to yield the secreted, biologically active 17-kDa form. Both murine and human forms of EMAP-II display an aspartate in the P-1 position. Processing of EMAP-II in this manner would produce a 18 kDa polypeptide with 165 amino acids.

Kao et al (supra) reported that EMAP-II promotes thrombohemorrhage and increases the vascular permeability of tumors. Purified, recombinant mature EMAP-II activates endothelial cells (ECs) and results in elevation of cytosolic free calcium concentration, release of von Willebrand factor, induction of tissue factor, and expression of the adhesion molecules, E-selectin and P-selectin. Neutrophils (PMNs) exposed to EMAP-II also demonstrate elevated cytosolic free calcium concentration as well as myeloperoxidase generation and chemotactic mobility. EMAP-II also activates mononuclear phagocytes (MPs) by inducing expression of tumor necrosis factor-α (TNF), increasing MP tissue factor activity, stimulating chemotaxis, moderately inducing elaboration of IL-8 and slightly elevating cytosolic free calcium concentration. In addition, preliminary evidence indicates that MPs produce EMAP-II when treated with LPS, which suggests that EMAP-II plays a role in endotoxin-mediated host responses and the proinflammatory cytokine cascade.

Mice given a systemic infusion of 10 μg EMAP-II derived from Meth A tumors developed the following: 1) systemic toxicity, including lethargy, decreased food/water intake, and ruffled body hair; 2) pulmonary congestion, including labored, rapid respiration and arrest of circulating leukocytes and other inflammatory cells in the pulmonary vasculature with concurrent increase of myeloperoxidase activity; and 3) the appearance of TNFα, interleukin-1 and -6 in the plasma. In another study, Kao et al found that a single intra-tumor injection of EMAP-II into Meth A sarcomas induced acute thrombohemorrhage in 67% of the animals, infiltration of tumor with PMNs, and partial tumor regression. Although local injection of EMAP-II alone into a TNF-resistant murine mammary carcinoma had no effect, when injection of EMAP-II was followed 15 h later by systemic administration of TNF, the tumor regressed following acute inflammatory infiltration by PMNs and thrombohemorrhage. In pilot studies, Kao et al found that a similar priming effect occurred when the tumor bed of B16 melanomas and human fibrosarcomas was treated with EMAP-II.

Kao et al (1994 J Biol Chem 269: 9774–82) further suggest that the amino terminus of cytokines may have a role in chemoattractant activity and the mobilization of intracellular calcium. For instance, mutagenesis of amino acids in the $NH_2$-terminus of IL-8 rendered the molecule incapable of mobilizing calcium in neutrophils and lowered its ability to compete with native IL-8 for neutrophil IL-8 receptors. Kao J et al created a synthetic oligopeptide comprising 15 residues from the N-terminal region of EMAP-II. This peptide induced directional migration and elevation of cytosolic free calcium concentration in MPs and PMNs and stimulated peroxidase release in PMNs. In addition, oligopeptide-albumin conjugates injected into the mouse footpad elicited infiltration of inflammatory cells. In contrast, a peptide from the C-terminus of EMAP-II had no effect.

In binding assays, the $NH_2$-terminal oligopeptide bound specifically to MPs. Binding of $I_{125}$-labeled oligopeptide was saturable and blockable using either unlabeled EMAP-II derived peptides or intact EMAP-II. However, other peptides such as IL-1, TNF, and formyl-methionyl-leucinyl-phenylalanine had no blocking effect. When cross-linked to human MPs, $I_{125}$-EMAPP-II derived peptide demonstrated a band, approximately 73 kDa, on reduced sodium dodecyl sulfate-polyacrylamide gel electrophoresis supporting the existence of a specific receptor. In addition, specific binding of the derived peptide to human PMNs and murine RAW cells was demonstrated.

Cytokines could satisfy a need in the art by providing new ways to treat cancers. The systemic infusion of cytokines appears to destroy specific cell types in the vasculature of B16 melanomas and fibrosarcomas. This destruction results in diminished blood flow, increased permeability to host effector cells and increased thrombohemorrhage. Utilization of the response to cytokine infusion is of particular therapeutic interest and has great value in the treatment of those cancers which are resistant to conventional treatments.

SUMMARY OF THE INVENTION

The present invention discloses a novel monocyte activating cytokine, hereinafter referred to as MAC, which shares features with other proteins involved in cell proliferation, differentiation and chemotaxis. Accordingly, the invention features a substantially purified MAC, as shown in the amino acid sequence of SEQ ID NO:1.

The novel monocyte activating cytokine has 301 amino acid residues, a number of conserved cysteines, $C_{197}$, $C_{215}$, $C_{274}$, and $C_{292}$, and three potential N-linked glycosylation sites, $N_8$, $N_{59}$, and $N_{299}$. In addition, MAC has 44% identity to endothelial-monocyte activating polypeptide II (EMAP-II) as well as similarities in hydrophobicity and isoelectric point.

One aspect of the invention features isolated and substantially purified polynucleotides which encode MAC. In a particular aspect, the polynucleotide is the nucleotide sequence of SEQ ID NO:2. In addition, the invention features polynucleotide sequences that hybridize under stringent conditions to SEQ ID NO:2.

The invention further relates to the nucleic acid sequence encoding MAC, oligonucleotides, peptide nucleic acids (PNA), fragments, portions or antisense molecules thereof. The present invention also relates, in part, to the inclusion of the nucleic acid sequence encoding MAC in an expression vector which can be used to transform host cells.

The present invention also relates to a method for producing MAC or a fragment thereof. It contemplates the delivery of purified MAC, alone or in a pharmaceutically acceptable excipient, to cancerous cells or tissues. It also encompasses antibodies which bind specifically to MAC and can be used to monitor testing of cytokine-sensitive tumors.

BRIEF DESCRIPTION OF THE FIGURES

FIGS. 1A, 1B, 1C and 1D show the amino acid sequence (SEQ ID NO:1) and nucleic acid sequence (SEQ ID NO:2) of the novel monocyte activating cytokine. The alignment was produced using MACDNASIS software (Hitachi Software Engineering Co Ltd, San Bruno Calif.).

Figure 2B:
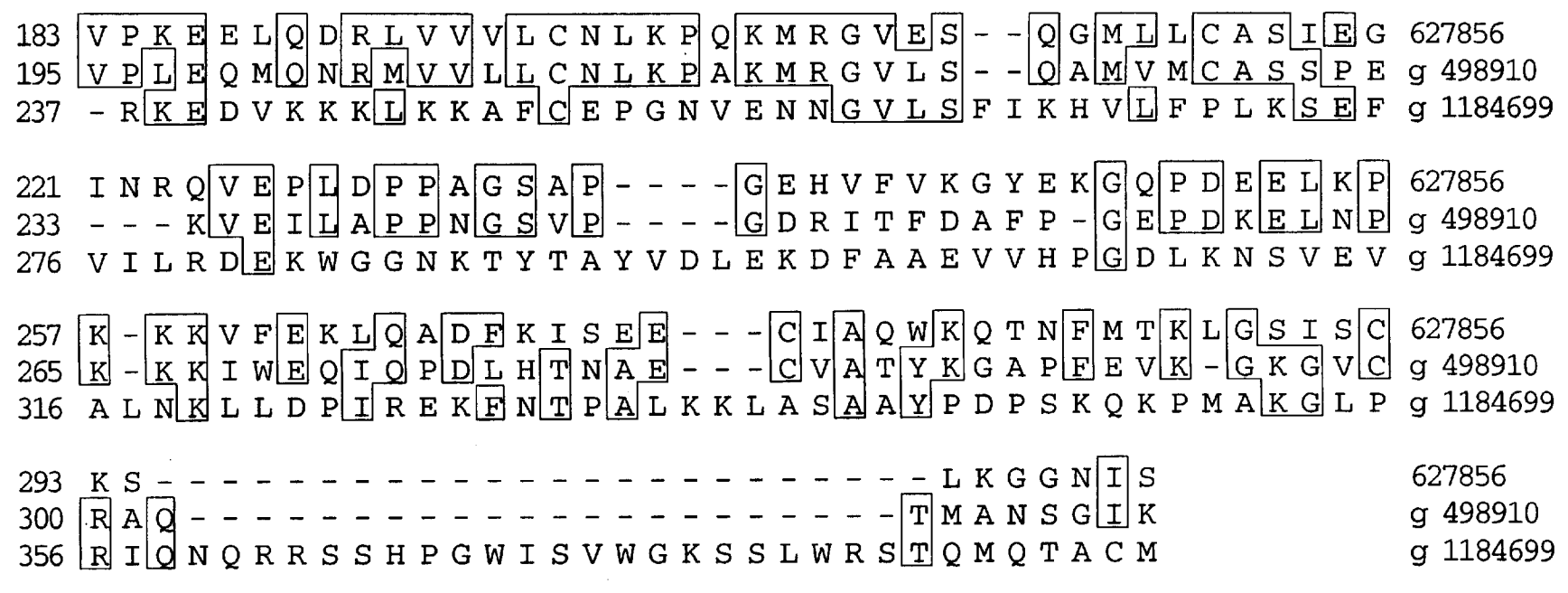

FIGS. 2A and 2B shows the amino acid sequence alignments among monocyte activating cytokine (627856; SEQ ID NO:1), GI 498910 (SEQ ID NO:3; Kao J et al supra), and GI 1184699 (SEQ ID NO:4; Ribas de Pouplana L (1966) Proc Nat Acad Sci 93:166–170). These alignments were produced using the multisequence alignment program of DNAStar software (DNAStar Inc, Madison Wis.).

FIGS. 5A and 5B show the secondary structure for the monocyte activating cytokine, SEQ ID NO:1 (MacDNAsis software).

DESCRIPTION OF THE INVENTION

Definitions

Figure 3:
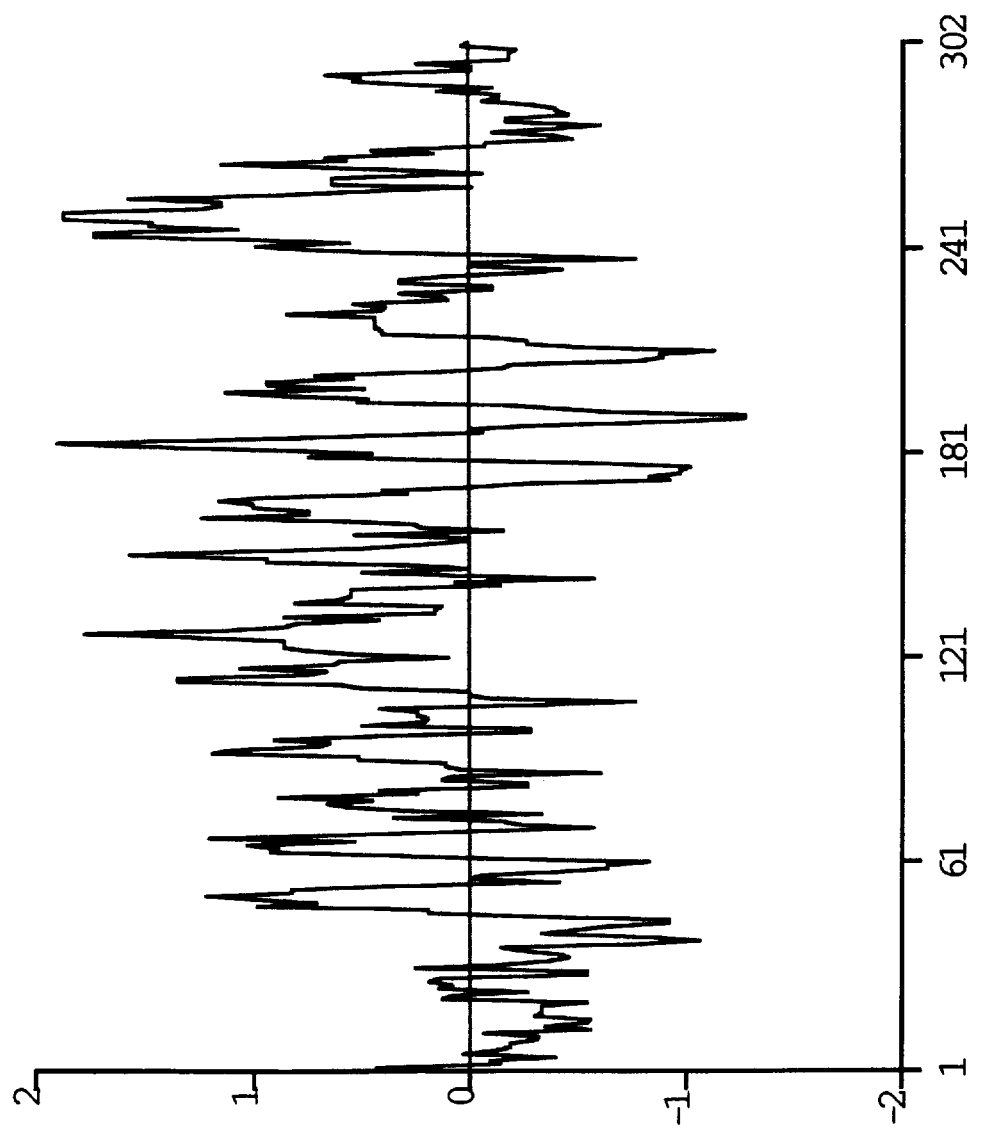
FIG. 3 shows the hydrophobicity plot for monocyte activating cytokine (SEQ ID NO:1 (MACDNASIS software). The X axis reflects amino acid position, and the negative Y axis, hydrophobicity.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring MAC.

A "substitution" results from the replacement of one or more nucleotides or amino acids by different nucleotides or amino acids, respectively.

As used herein, MAC refers to the amino acid sequence of substantially purified MAC obtained from any species, particularly mammalian, including bovine, ovine, porcine, murine, equine, and preferably human, from any source whether natural, synthetic, semi-synthetic or recombinant.

A "variant" of MAC is defined as an amino acid sequence which differs by one or more amino acids. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "biologically active" refers to a MAC having structural, regulatory or biochemical functions of a naturally occurring MAC. Likewise, "immunologically active" defines the capability of the natural, recombinant or synthetic MAC, or any oligopeptide thereof, to induce a specific immune response in appropriate animals or cells and to bind with specific antibodies.

The term "derivative" as used herein refers to the chemical modification of a nucleic acid encoding MAC or the encoded MAC. Illustrative of such modifications would be replacement of hydrogen by an alkyl, acyl, or amino group. A nucleic acid derivative would encode a polypeptide which retains essential biological characteristics of natural MAC.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification is defined as the production of additional copies of a nucleic acid sequence and is generally carried out using polymerase chain reaction technologies well known in the art (Dieffenbach C W and G S Dveksler (1995) *PCR Primer, a Laboratory Manual*, Cold Spring Harbor Press, Plainview N.Y.).

"Stringency" typically occurs in a range from about Tm-5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

Description

The consensus nucleotide sequence, disclosed herein, encodes a monocyte activating cytokine of 301 amino acid residues (FIGS. 1A, 1B, 1C and 1D) with an isoelectric point of 7.12. The consensus sequence is based on the extension and assembly of the following Incyte clones: 627856, 399219 (PITUNOT02), 458325 (KERANOT01), 821830 (KERANOT02), and 1367313 (SCORNON02). The aspartate residue at position 142 is analogous to a highly conserved prohormone processing site present in IL-1β, IL-8, von Willebrands Antigen II, and EMAP-II. Amino acid sequence homology in the $NH_2$-terminus of the mature protein strongly suggests that MAC functions as a cytokine and can mobilize intracellular calcium in ECs, PMNs and MPs.

The amino acid alignments of the MAC and EMAP-II are shown in FIGS. 2A and 2B. Using the numbers for MAC at the top of the figure as a reference, the following cysteine residues are conserved: $C_{197}$, $C_{215}$, $C_{274}$, and $C_{292}$. MAC has three potential N-linked glycosylation sites, $N_8$, $N_{59}$, and $N_{299}$, although the first two would not be present in the mature protein. The hydrophobicity plot for MAC aligns with that for EMAP-II further suggesting similar functions as secreted cytokines.

The MAC Coding Sequences

The nucleic acid and deduced amino acid sequences of MAC are shown in FIGS. 1A, 1B, 1C and 1D. In accordance with the invention, any nucleic acid sequence which encodes MAC can be used to generate recombinant molecules which express MAC. In a specific embodiment described herein, a partial sequence encoding MAC was first isolated as Incyte Clone 627856 from a macrophage cDNA library (KIDNNOT05).

It will be appreciated by those skilled in the art that as a result of the degeneracy of the genetic code, a multitude of MAC-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence encoding naturally occurring MAC, and all such variations are to be considered as being specifically disclosed.

Although nucleotide sequences which encode MAC and its variants are preferably capable of hybridizing to the nucleotide sequence of the naturally occurring sequence under appropriately selected conditions of stringency, it may be advantageous to produce nucleotide sequences encoding MAC or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding MAC and its derivatives without altering the encoded amino acid sequences include the production of RNA transcripts having more desirable properties, such as a greater half-life, than transcripts produced from the naturally occurring sequence.

A DNA sequence, or portions thereof, encoding MAC and its derivatives may be produced entirely by synthetic chemistry, after which the synthetic gene may be inserted into any of the many available DNA vectors and cell systems using reagents that are generally available. Moreover, synthetic chemistry may be used to introduce mutations into a sequence encoding MAC or any portion thereof.

Also included within the scope of the present invention are polynucleotide sequences that are capable of hybridizing to the nucleotide sequence of SEQ ID NO:2 under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and may be used at a defined "stringency".

Altered nucleic acid sequences encoding MAC which may be used in accordance with the invention include deletions, insertions or substitutions of different nucleotides resulting in a polynucleotide that encodes the same or a functionally equivalent MAC. The protein may also show deletions, insertions or substitutions of amino acid residues which produce a silent change and result in a functionally equivalent MAC. Deliberate amino acid substitutions may be made on the basis of similarity in polarity, charge, solubility, hydrophobicity, hydrophilicity, and/or the amphipathic nature of the residues as long as the biological activity of MAC is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; and serine, threonine phenylalanine, and tyrosine.

Included within the scope of the present invention are alleles encoding MAC. As used herein, an "allele" or "allelic sequence" is an alternative form of the nucleic acid sequence encoding MAC. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing may be used which are well known in the art and employ such enzymes as the Klenow fragment of DNA polymerase I, SEQUENASE (US Biochemical Corp, Cleveland Ohio), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the MICROLAB 2200 (Hamilton, Reno Nev.), Peltier thermal cycler (PTC200; MJ Research, Watertown Mass.), and the ABI 377 DNA sequencers (Perkin Elmer).

Extending the Polynucleotide Sequence

The polynucleotide sequence encoding MAC may be extended utilizing partial nucleotide sequence and various methods known in the art to detect upstream sequences such as promoters and regulatory elements. For example, the method of Gobinda et al (1993; PCR Methods Applic 2:318–22) involves "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO 4.06 primer analysis software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) may also be used as a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequence is walking PCR (Parker J D et al (1991) Nucleic Acids Res 19:3055–60), and which involves targeted gene walking. Alternatively, PCR, nested primers, PROMOTER-FINDER (Clontech, Palo Alto Calif.) and PROMOTER-FINDER libraries can be used to walk in genomic DNA. This process avoids the need to screen libraries and is useful in finding intron/exon junctions.

Preferred libraries for screening for full length cDNAs are those which have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze either the size or confirm the nucleotide sequence in sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER and SEQUENCE NAVIGATOR from Perkin Elmer) and the entire process from loading of samples to computer analysis and electronic data display is computer-controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, polynucleotide sequences which encode MAC, fragments of the polypeptide, fusion proteins, or functional equivalents thereof may be used in recombinant DNA molecules that direct the expression of MAC in appropriate host cells. Due to the inherent degeneracy of the genetic code, other DNA sequences which encode substantially the same or a functionally equivalent amino acid sequence may be used to clone and express MAC. As will be understood by those of skill in the art, it may be advantageous to produce MAC-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of MAC expression or to produce recombinant RNA transcripts having desirable properties, such as a longer half-life, than transcripts produced from naturally occurring sequence.

The nucleotide sequences of the present invention can be engineered in order to alter a MAC-encoding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant MAC-encoding sequence may be ligated to a heterologous sequence to encode a fusion protein. For example, for screening of peptide libraries for inhibitors of MAC activity, it may be useful to encode a chimeric MAC protein that is recognized by a commercially available antibody. A fusion protein may also be engineered to contain a cleavage site located between a MAC and the heterologous protein sequence so that the MAC may be cleaved and substantially purified away from the heterologous moiety.

In an alternate embodiment of the invention, the sequence encoding MAC may be synthesized, whole or in part, using chemical methods well known in the art (see Caruthers M H et al (1980) Nuc Acids Res Symp Ser 215–23, Horn T et al (1980) Nuc Acids Res Symp Ser 225–32, etc). Alternatively, the protein itself may be produced using chemical methods to synthesize a MAC amino acid sequence, whole or in part. For example, peptide synthesis can be performed using various solid-phase techniques (Roberge J Y et al (1995) Science 269:202–204) and automated synthesis may be achieved, for example, using the ABI 431A peptide synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles*, W H Freeman and Co, New York N.Y.). The composition of the synthetic peptides may be confirmed by amino acid analysis or sequencing (eg, the Edman degradation procedure; Creighton, supra). Additionally the amino acid sequence of MAC, or any part thereof, may be altered during direct synthesis and/or combined using chemical methods with sequences from other proteins, or any part thereof, to produce a variant polypeptide.

Expression Systems

In order to express a biologically active MAC, the nucleotide sequence encoding MAC or its functional equivalent, is inserted into an appropriate expression vector, ie, a vector which contains the necessary elements for the transcription and translation of the inserted coding sequence.

Methods which are well known to those skilled in the art can be used to construct expression vectors containing a MAC-encoding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel F M et al (1989) *Current Protocols in Molecular Biology*, John Wiley & Sons, New York N.Y.

A variety of expression vector/host systems may be utilized to contain and express a MAC-encoding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla Calif.) or pSport1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of the sequence encoding MAC, vectors based on SV40 or EBV may be used with an appropriate selectable marker.

In bacterial systems, a number of expression vectors may be selected depending upon the use intended for MAC. For example, when large quantities of MAC are needed for the induction of antibodies, vectors which direct high level expression of fusion proteins that are readily purified may be desirable. Such vectors include, but are not limited to, the multifunctional *E. coli* cloning and expression vectors such as BLUESCRIPT (Stratagene), in which the sequence encoding MAC may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding MAC may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Hill *Yearbook of Science and Technology* (1992) McGraw Hill New York N.Y., pp 191–196 or Weissbach and Weissbach (1988) *Methods for Plant Molecular Biology*, Academic Press, New York N.Y., pp 421–463.

An alternative expression system which may be used to express MAC is an insect system. In one such system, *Autographa californica* nuclear polyhedrosis virus (AcNPV) is used as a vector to express foreign genes in *Spodoptera frugiperda* cells or in Trichoplusia larvae. The sequence encoding MAC may be cloned into a nonessential region of the virus, such as the polyhedrin gene, and placed under control of the polyhedrin promoter. Successful insertion of the sequence encoding MAC will render the polyhedrin gene inactive and produce recombinant virus lacking coat protein coat. The recombinant viruses are then used to infect *S. frugiperda* cells or Trichoplusia larvae in which MAC is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a sequence encoding MAC may be ligated into an adenovirus transcription/translation complex consisting of the late promoter and tripartite leader sequence. Insertion in a nonessential E1 or E3 region of the viral genome will result in a viable virus capable of expressing in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a sequence encoding MAC. These signals include the ATG initiation codon and adjacent sequences. In cases where the sequence encoding MAC, its initiation codon and upstream sequences are inserted into the most appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express MAC may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic, or herbicide resistance can be used as the basis for selection; for example, dhfr, which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the sequence encoding MAC is inserted within a marker gene sequence, recombinant cells containing the sequence encoding MAC can be identified by the absence of marker gene function. Alternatively, a marker gene can be placed in tandem with the sequence encoding MAC under the control of a single promoter. Expression of the marker gene in response to induction or selection usually indicates expression of the tandem sequence as well.

Alternatively, host cells which contain the sequence encoding MAC and expressing MAC may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding MAC can be detected by DNA-DNA or DNA-RNA hybridization or amplification using probes, portions or fragments of the sequence encoding MAC. Nucleic acid amplification based assays involve the use of oligonucleotides or oligomers based on the nucleic acid sequence to detect transformants containing DNA or RNA encoding MAC. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of MAC, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on MAC is preferred, but a competitive binding assay may be employed. These and other assays are described, among other places, in Hampton R et al (1990, *Serological Methods, a Laboratory Manual*, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting related sequences include oligolabeling, nick translation, end-labeling or PCR amplification using a labeled nucleotide. Alternatively, the MAC-encoding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567, incorporated herein by reference.

Purification of MAC

Host cells transformed with a nucleotide sequence encoding MAC may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing MAC-encoding sequence can be designed with signal sequences which direct secretion of MAC through a prokaryotic or eukaryotic cell membrane. Other recombinant constructions may join the sequence encoding MAC to nucleotide sequence encoding a polypeptide domain which will facilitate purification of soluble proteins (Kroll D J et al (1993) DNA Cell Biol 12:441–53; cf discussion of vectors infra containing fusion proteins).

MAC may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and MAC is useful to facilitate purification. One such expression vector provides for expression of a fusion protein comprising the sequence encoding MAC and nucleic acid sequence encoding 6 histidine residues followed by thioredoxin and an enterokinase cleavage site. The histidine residues facilitate purification while the enterokinase cleavage site provides a means for purifying MAC from the fusion protein.

In addition to recombinant production, fragments of MAC may be produced by direct peptide synthesis using solid-phase techniques (cf Stewart et al (1969) *Solid-Phase Peptide Synthesis*, W H Freeman Co, San Francisco; Merrifield J (1963) J Am Chem Soc 85:2149–2154). In vitro protein synthesis may be performed using manual techniques or by automation. Automated synthesis may be achieved, for example, using the Applied Biosystems 431A peptide synthesizer (Perkin Elmer, Foster City Calif.) in accordance with the instructions provided by the manufacturer. Various fragments of MAC may be chemically synthesized separately and combined using chemical methods to produce the full length molecule.

Uses of MAC

Based on its amino acid sequence similarity to EMAP-II and its association with endothelial cells, lymphocytes, monocytes, immortalized cell lines and tumors, MAC appears to play a role in immune response. Therefore, MAC, its fragments or derivatives may be used therapeutically in the treatment of disease states such as cancers, immune deficiencies, or excessive immune responses.

A therapeutic composition comprising purified MAC may be used in the treatment of cancer. In particular, purified MAC may be administered to induce host effector cell infiltration and tumor regression. MAC may also be administered systemically for the treatment of melanomas and cytokine-sensitive tumors or used to prime TNFα-resistant tumors by direct injection into the tumor followed by systemic administration of TNF.

A therapeutic composition comprising MAC may be used in the prevention and treatment of disease conditions which compromise the immune system. Examples include, but are not limited to, HIV infection, Job-Buckley syndrome, lazy leukocyte syndrome, acquired agranulocytosis, and Chediak-Higashi syndrome. Although the pathologies of these diseases differ, common features include impairment of the immune system with subsequent predisposition to infections. Administration of minute amounts of MAC may be used to attract and activate leukocytes and monocytes and to induce expression of molecules necessary for leukocyte adhesion in vascular endothelial cells. Therapeutic administration of MAC to a site of infection could recruit leukocytes and monocytes to the site to fight the infection.

In another embodiment of the present invention, antagonists, inhibitors or anti-MAC antibodies, capable of neutralizing the activity of MAC, may be used to modulate or treat conditions or disease states characterized by excessive leukocyte or monocyte activity. Such conditions include, but are not limited to, septic shock or alpha-1-antitrypsin (α1AT) deficiency. In α1AT deficiency, the potent protease elastase, which is normally secreted by neutrophils and degraded by α1AT, is not deactivated due to low serum levels of α1AT. The excess elastase causes tissue damage and inflammation, particularly in the lungs and may result in emphysema. While intravenous administration of α1AT is standard and effective, administration of MAC antagonists, inhibitors or antibodies by inhalation could result in deactivation and dispersal of neutrophils, ameliorating acute inflammation and tissue destruction. Other disease states which result from similar excessive leukocyte or monocyte activity could be treated in a similar manner.

MAC Antibodies

MAC-specific antibodies are useful for the diagnosis and treatment of conditions and diseases associated with expression of MAC. Such antibodies include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

The portion of MAC used for antibody induction does not need to have biological activity; however, it must be antigenic. Peptides used to induce specific antibodies may have an amino acid sequence consisting of at least five amino acids, and preferably at least 10 amino acids. Preferably, they should mimic a portion of the amino acid sequence of the natural protein and may contain the entire amino acid sequence of a small, naturally occurring molecule. Short stretches of MAC amino acids may be fused with those of another protein such as keyhole limpet hemocyanin and antibody produced against the chimeric molecule. Procedures well known in the art can be used for the production of antibodies to MAC.

For the production of antibodies, various hosts including goats, rabbits, rats, mice, etc may be immunized by injection with MAC or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to MAC may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce MAC-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for MAC may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between MAC and its specific antibody and the measurement of complex formation. A two-site, monoclonal-based immunoassay utilizing monoclonal antibodies reactive to two noninterfering epitopes on a specific MAC protein is preferred, but a competitive binding assay may also be employed. These assays are described in Maddox D E et al (1983, J Exp Med 158:1211).

Diagnostic Assays Using MAC Specific Antibodies

Particular MAC antibodies are useful for the diagnosis of conditions or diseases characterized by expression of MAC or in assays to monitor patients being treated with MAC, its fragments, agonists or inhibitors. Diagnostic assays for MAC include methods utilizing the antibody and a label to detect MAC in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring MAC, using either polyclonal or monoclonal antibodies specific for the respective protein are known in the art. Examples include enzyme-linked immunosorbent assay (ELISA), radioimmunoassay (RIA), and fluorescent activated cell sorting (FACS). A two-site, monoclonal-based immunoassay utilizing monoclonal antibodies reactive to two non-interfering epitopes on MAC is preferred, but a competitive binding assay may be employed. These assays are described, among other places, in Maddox, D E et al (1983, J Exp Med 158:1211).

In order to provide a basis for diagnosis, normal or standard values for MAC expression must be established. This is accomplished by combining body fluids or cell extracts taken from normal subjects, either animal or human, with antibody to MAC under conditions suitable for complex formation which are well known in the art. The amount of standard complex formation may be quantified by comparing various artificial membranes containing known quantities of MAC with both control and disease samples from biopsied tissues. Then, standard values obtained from normal samples may be compared with values obtained from samples from subjects potentially affected by disease. Deviation between standard and subject values establishes the presence of disease state.

Drug Screening

MAC, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between MAC and the agent being tested, may be measured.

Another technique for drug screening which may be used for high throughput screening of compounds having suitable binding affinity to the MAC is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of MAC and washed. Bound MAC is then detected by methods well known in the art. Substantially purified MAC can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding MAC specifically compete with a test compound for binding MAC. In this manner, the antibodies can be used to detect the presence of any peptide which shares one or more antigenic determinants with MAC.

Uses of the Polynucleotide Encoding MAC

A polynucleotide sequence encoding MAC or any part thereof may be used for diagnostic and/or therapeutic purposes. For diagnostic purposes, the sequence encoding MAC of this invention may be used to detect and quantitate gene expression in biopsied tissues in which MAC may be expressed in response to oncogenes. The diagnostic assay is useful to distinguish between absence, presence, and excess expression of MAC and to monitor regulation of MAC levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding MAC or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring MAC, alleles or related sequences.

Probes may also be used for the detection of related sequences and should preferably contain at least 50% of the nucleotides from any of these MAC-encoding sequences. The hybridization probes of the subject invention may be derived from the nucleotide sequence of SEQ ID NO:2 or from genomic sequence including promoter, enhancer elements and introns of the naturally occurring sequence encoding MAC. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs include the cloning of nucleic acid sequences encoding MAC or MAC derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostic Use

Polynucleotide sequences encoding MAC may be used for the diagnosis of conditions or diseases with which the expression of MAC is associated. For example, polynucleotide sequences encoding MAC may be used in hybridization or PCR assays of fluids or tissues from biopsies to detect MAC expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The MAC-encoding nucleotide sequences disclosed herein provide the basis for assays that detect activation or induction associated with inflammation or disease. The nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding MAC in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for MAC expression must be established. This is accomplished by combining body fluids or cell extracts taken from normal subjects, either animal or human, with MAC, or a portion thereof, under conditions suitable for hybridization or amplification. Standard hybridization may be quantified by comparing the values obtained for normal subjects with a dilution series of MAC run in the same experiment where a known amount of substantially purified MAC is used. Standard values obtained from normal samples may be compared with values obtained from samples from patients affected by MAC-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, may be used as described in U.S. Pat. Nos. 4,683, 195 and 4,965,188 to provide additional uses for oligonucleotides based upon the sequence encoding MAC. Such oligomers are generally chemically synthesized, but they may be generated enzymatically or produced from a recombinant source. Oligomers generally comprise two nucleotide sequences, one with sense orientation (5'→3') and one-with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P C et al 1993 J Immunol Methods 159:235–44) or biotinylating (Duplaa C et al 1993 Anal Biochem 212:229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or calorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to EMAP-II and its expression profile, the polynucleotide encoding MAC disclosed herein may be useful in the treatment of immune difficiency diseases.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense of the sequence encoding MAC. See, for example, the techniques described in Sambrook et al (supra) and Ausubel et al (supra).

The polynucleotides comprising full length cDNA sequence and/or its regulatory elements enable researchers to use the sequence encoding MAC as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding MAC can be turned off by transfecting a cell or tissue with expression vectors which express high levels of a desired MAC fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of the sequence encoding MAC, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of the sequence encoding MAC.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding MAC. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient as presented in U.S. Pat. Nos. 5,399,493 and 5,437,994, disclosed herein by reference. Delivery by transfection and by liposome are quite well known in the art.

Furthermore, the nucleotide sequences encoding MAC disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence encoding MAC can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a sequence encoding MAC on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of MAC, such labeling would include amount, frequency and method of administration.

Therapeutically Effective Dose

Pharmaceutical compositions suitable for use in the present invention include compositions wherein the active ingredients are contained in an effective amount-to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, which can be expressed as the ratio LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that MAC can be used as a therapeutic molecule to force differentiation, stopping the cell cycle which contributes to the growth of cancerous cells or tissues.

The examples below are provided to illustrate the subject invention and are not included for the purpose of limiting the invention.

EXAMPLES

I cDNA Library Construction

The KIDNNOT05 cDNA library was constructed from tissue removed from a female infant kidney with anoxia (lot #RU95-04-0274; International Institute of Advanced Medicine, Exton Pa.). The frozen tissue was immediately homogenized and cells lysed with a POLYTRON PT-3000 (Brinkmann Instruments Inc, Westbury N.Y.) in a guanidinium isothiocyanate solution. Lysates were then loaded on a 5.7 M CsCl cushion and ultracentrifuged in a SW28 swinging bucket rotor for 18 hours at 25,000 rpm at ambient temperature. The RNA was extracted once with acid phenol at pH 4.0 and precipitated with 0.3 M sodium acetate and 2.5 volumes of ethanol, resuspended in DEPC-treated water and DNase treated for 25 min at 37° C. The reaction was stopped with an equal volume of pH 8.0 phenol, and the RNA was as above. The RNA was isolated using the OLIGOTEX kit (QIAGEN Inc, Chatsworth Calif.) and used to construct the cDNA library.

The RNA was handled according to the recommended protocols in the SUPERSCRIPT plasmid system for cDNA synthesis and plasmid cloning (catalog #18248-013; Gibco/BRL). cDNAs were fractionated on a SEPHAROSE CL4B column (catalog #275105, Pharmacia), and those cDNAs exceeding 400 bp were ligated into PSPORT I. The plasmid PSPORT I was subsequently transformed into DH5α competent cells (Cat. #18258-012, Gibco/BRL).

II Isolation and Sequencing of cDNA Clones

Plasmid DNA was released from the cells and purified using the Miniprep Kit (Catalogue # 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog # 22711, LIFE TECHNOLOGIES, Gaithersburg Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and A R Coulson (1975; J Mol Biol 94:441f), using a MICROLAB 2200 (Hamilton, Reno Nev.) in combination with four Peltier Thermal Cyclers (PTC200 from MJ Research, Watertown Mass.) and Applied Biosystems 377 or 373 DNA sequencing systems (Perkin Elmer), and reading frame was determined.

III Homology Searching of cDNA Clones and Their Deduced Proteins

Each cDNA was compared to sequences in GenBank using a search algorithm developed by Applied Biosystems and incorporated into the INHERIT- 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 sequence analysis system in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al. supra).

Analogous computer techniques using BLAST (Altschul S F 1993 and 1990, supra) are used to search for identical or related molecules in nucleotide databases such as the GenBank or LIFESEQ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of the Sequence Encoding MAC

The nucleic acid sequence of SEQ ID NO:2 is used to design oligonucleotide primers for extending a partial nucleotide sequence to full length or for obtaining 5'sequence from genomic libraries. One primer is synthesized to initiate extension in the antisense direction (XLR) and the other is synthesized to extend sequence in the sense direction (XLF). Primers allow the extension of the known sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQUICK (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent *E. coli* cells (in 40 μl of appropriate media) are transformed with 3 μl of ligation mixture and cultured in 80 μl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 mCi of [$\gamma$-$^{32}$P] adenosine triphosphate (Amersham, Chicago Ill.) and T4 polynucleotide kinase (DuPont NEN, Boston Mass.). The labeled oligonucleotides are substantially purified with SEPHADEX G-25 super fine resin column (Pharmacia). A portion containing 10 counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (NYTRAN Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Kodak, Rochester N.Y.) is exposed to the blots or the blots are exposed in a PHOSPHOIMAGER cassette (Molecular Dynamics, Sunnyvale Calif.), hybridization patterns are compared visually.

VII Antisense Molecules

The sequence encoding MAC, or any part thereof, is used to inhibit in vivo or in vitro expression of naturally occurring sequence. Although use of antisense oligonucleotides, comprising about 20 base-pairs, is specifically described, essentially the same procedure is used with larger cDNA fragments. An oligonucleotide complementary to the coding sequence of MAC as shown in FIGS. 1A, 1B, 1C, and 1D are used to inhibit expression of naturally occurring sequence. The complementary oligonucleotide is designed from the most unique 5' sequence as shown in FIGS. 1A, 1B, 1C, and 1D and used either to inhibit transcription by preventing promoter binding to the upstream nontranslated sequence or translation of an MAC-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A, 1B, 1C and 1D.

VIII Expression of MAC

Expression of the MAC is accomplished by subcloning the cDNAs into appropriate vectors and transfecting the vectors into host cells. In this case, the cloning vector, pSport, previously used for the generation of the cDNA library is used to express MAC in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length MAC. The signal sequence directs the secretion of MAC into the bacterial growth media which can be used directly in the following assay for activity.

IX Assay for MAC Activity

Chemotactic activity is measured in a 48-well microchemotaxis chamber. In each well, two compartments are separated by a filter that allows the passage of cells from one compartment into the other in response to a chemical gradient. Cell culture medium into which MAC has been secreted is placed on one side of a polycarbonate filter, and peripheral blood cells are suspended in the same media on the opposite side of the filter. After sufficient incubation time to allow diffusion of MAC, the filters are recovered and specific cell types, eg, monocytes, adhering to the side of the filter facing the cytokine are identified and counted.

Cytokine specificity may be determined by performing the assay on fractionated, enriched populations of neutrophils, mononuclear cells, monocytes or lymphocytes obtained by density gradient centrifugation. Specific T cell populations can be assayed following purification using CD8+ and CD4+ specific antibodies for negative selection.

To assay non-chemotactic activity, a method for the monitoring of myeloperoxidase can be found in Menegazzi R et al (1992) J Leuk Biol 52:619–624.

X Production of MAC Specific Antibodies

Figure 4:
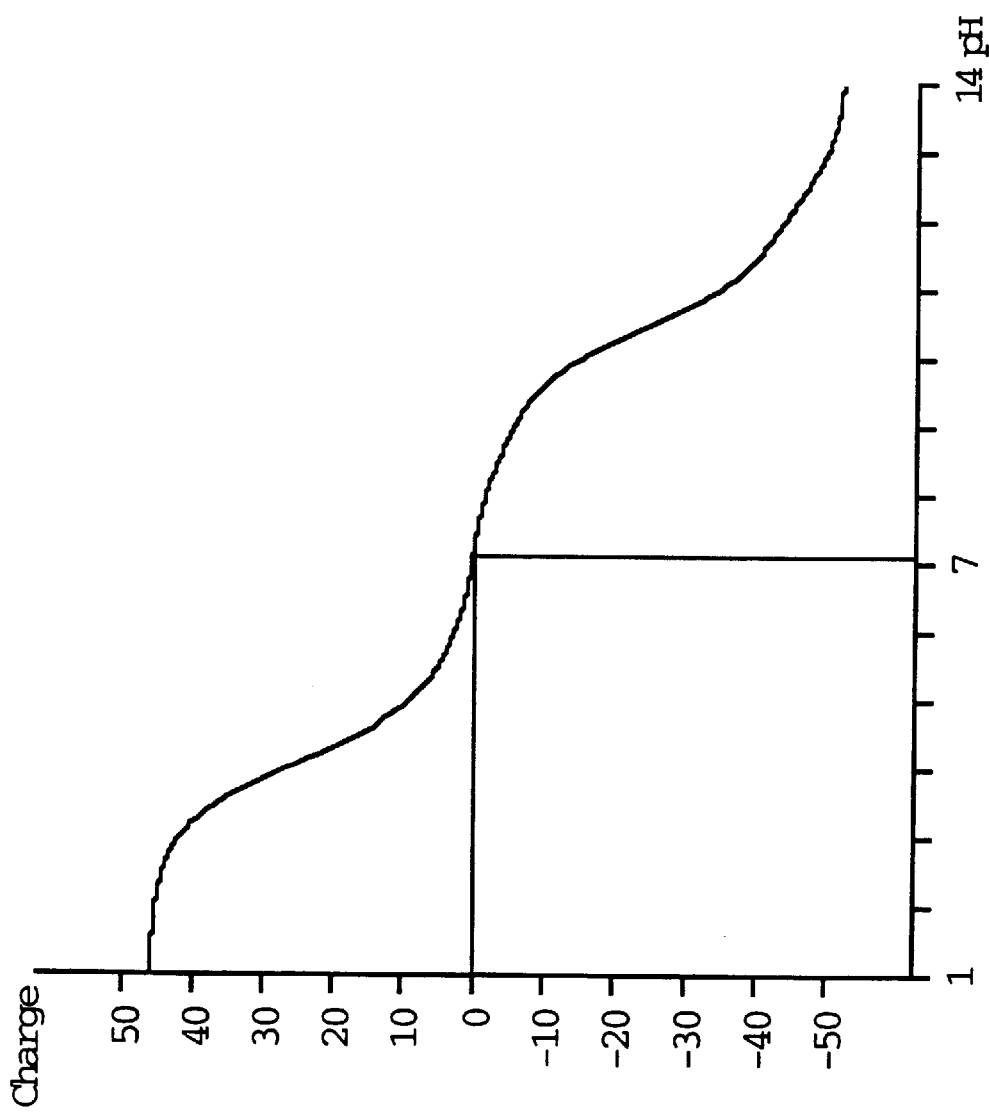
FIG. 4 shows the isoelectric plot for monocyte activating cytokine, SEQ ID NO:1 (MacDNAsis software).

MAC substantially purified using PAGE electrophoresis (Sambrook, supra) is used to immunize rabbits and to produce antibodies using standard protocols. The amino acid sequence translated from MAC is analyzed using DNASTAR software (DNAStar Inc) to determine regions of high immunogenicity and a corresponding oligopeptide is synthesized and used to raise antibodies by means known to those of skill in the art. Analysis to select appropriate epitopes, such as those near the C-terminus or in hydrophilic regions (shown in FIGS. 4, 5A and 5B) is described by Ausubel F M et al (supra).

Typically, the oligopeptides are 15 residues in length, synthesized using an Applied Biosystems 431A peptide synthesizer using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring MAC Using Specific Antibodies

Naturally occurring or recombinant MAC is substantially purified by immunoaffinity chromatography using antibodies specific for MAC. An immunoaffinity column is constructed by covalently coupling MAC antibody to an activated chromatographic resin such as CnBr-activated SEPHAROSE (Pharmacia Biotech). After the coupling, the resin is blocked and washed according to the manufacturer's instructions.

Membrane fractions from cells expressing MAC are prepared by methods well known in the art. Alternatively, a recombinant MAC fragment containing an appropriate signal sequence may be secreted in useful quantitiy into the medium in which transfected cells are grown.

A MAC-containing preparation is passed over the immunoaffinity column, and the column is washed under conditions that allow the preferential absorbance of MAC (eg, high ionic strength buffers in the presence of detergent). The column is eluted under conditions that disrupt antibody/MAC binding (eg, a buffer of pH 2–3 or a high concentration of a chaotrope such as urea or thiocyanate ion), and MAC is collected.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

We claim:

1. A substantially purified polypeptide comprising at least a portion of the amino acid sequence of SEQ ID NO: 1.

2. A pharmaceutical composition comprising at least a portion of the amino acid sequence of SEQ ID NO: 1 and a pharmaceutically acceptable excipient.

* * * * *

UNITED STATES PATENT AND TRADEMARK OFFICE
CERTIFICATE OF CORRECTION

PATENT NO. : 6,090,377
DATED : Jul. 18, 2000
INVENTOR(S) : Olga Bandman, Roger Coleman, Janice Au-Young, Lynn E. Murry It is certified that error appears in the above-identified patent and that said Letters Patent are hereby corrected as shown below:

Col. 37, lines 32 and 33, delete "at least a portion of".
Col. 37, line 34, delete "at least a".
Col. 38, line 31, delete "portion of".

Signed and Sealed this

Seventeenth Day of April, 2001

Attest:

NICHOLAS P. GODICI

*Attesting Officer*     Acting Director of the United States Patent and Trademark Office

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 301 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY:
        (B) CLONE: Consensus (xi) SEQUENCE DESCRIPTION: SEQ ID NO:1:

```
Met Lys Pro Ser Pro Thr Gly Asn Cys Ser Leu Arg Val Ala Asn Leu
 1               5                  10                  15

Gln Pro His Pro Leu Pro Pro Gly Pro Ala Val Arg Thr Phe Asp Ala
                20                  25                  30

Ser Leu Leu Thr Glu Gly Ile Thr Val Ala Ser Leu Leu Pro Glu Phe
            35                  40                  45

Val Ile Leu Arg Asp Glu Lys Trp Gly Gly Asn Lys Thr Tyr Thr Ala
        50                  55                  60

Tyr Val Asp Leu Glu Lys Asp Phe Ala Ala Glu Val Val His Pro Gly
65                  70                  75                  80

Asp Leu Lys Asn Ser Val Glu Val Ala Leu Asn Lys Leu Leu Asp Pro
                85                  90                  95

Ile Arg Glu Lys Phe Asn Thr Pro Ala Leu Lys Lys Leu Ala Ser Ala
               100                 105                 110

Ala Tyr Pro Asp Pro Ser Lys Gln Lys Pro Met Ala Lys Gly Pro Ala
           115                 120                 125
```

```
Lys Asn Ser Glu Pro Glu Val Ile Pro Ser Arg Leu Asp Ile Arg
    130                 135                 140

Val Gly Lys Ile Ile Thr Val Glu Lys His Pro Asp Ala Asp Ser Leu
145                 150                 155                 160

Tyr Val Glu Lys Ile Asp Val Gly Glu Ala Glu Pro Arg Thr Val Val
                165                 170                 175

Ser Gly Leu Val Gln Phe Val Pro Lys Glu Leu Gln Asp Arg Leu
            180                 185                 190

Val Val Val Leu Cys Asn Leu Lys Pro Gln Lys Met Arg Gly Val Glu
            195                 200                 205

Ser Gln Gly Met Leu Leu Cys Ala Ser Ile Glu Gly Ile Asn Arg Gln
            210                 215                 220

Val Glu Pro Leu Asp Pro Pro Ala Gly Ser Ala Pro Gly Glu His Val
225                 230                 235                 240

Phe Val Lys Gly Tyr Glu Lys Gly Gln Pro Asp Glu Glu Leu Lys Pro
                245                 250                 255

Lys Lys Lys Val Phe Glu Lys Leu Gln Ala Asp Phe Lys Ile Ser Glu
            260                 265                 270

Glu Cys Ile Ala Gln Trp Lys Gln Thr Asn Phe Met Thr Lys Leu Gly
            275                 280                 285

Ser Ile Ser Cys Lys Ser Leu Lys Gly Gly Asn Ile Ser
    290                 295                 300

(2) INFORMATION FOR SEQ ID NO:2:

(i) SEQUENCE CHARACTERISTICS:
        (A) LENGTH: 1449 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:2:

GGCCCGCTGC GCTGAGACAC TGAAGGGGTG TCCGGGAGCT GCTGAAAGCG TGTAGACCTC      60

GCGACGGTCC CGCGGTAGAC ATCGATATAA GAAGTAATGG GCTGCCACAG AGCCCAAATT     120

CCCTGCTGTT CGACTGGCTT TGCAGAATTT TGACATGACT TACAGTGTGC AGTTTGGAGA     180

TCTTTGGCCA TCAATCCGTG TCAGTCTCCT CTCAGAGCAG AAGTATGGTG CACTGGTCAA     240

TAACTTTGCT GCCTGGGATC ATGTAAGTGC TAAGCTGGAG CAGCTGAGTG CCAAGGATTT     300

TGTGAATGAA GCCATCTCCC ACTGGGAACT GCAGTCTGAG GGTGGCCAAT CTGCAGCCCC     360

ATCCCCTGCC TCCTGGGCCT GCAGTCCGAA CCTTCGATGC TTCACTTTTG ACAGAAGGGA     420

TAACAGTCGC TTCCCTCCTG CCAGAGTTTG TGATCCTACG AGATGAGAAA TGGGGTGGAA     480

ACAAAACCTA CACAGCTTAC GTGGACCTGG AAAAGGACTT TGCTGCTGAA GTTGTACATC     540

CTGGAGACCT GAAGAATTCT GTTGAAGTCG CACTGAACAA GTTGCTGGAT CCAATCCGGG     600

AAAAGTTTAA TACCCCTGCC CTGAAAAAAC TGGCCAGCGC TGCCTACCCA GATCCCTCAA     660

AGCAGAAGCC AATGGCCAAA GGCCCTGCCA AGAATTCAGA ACCAGAGGAG GTCATCCCAT     720

CCCGGCTGGA TATCCGTGTG GGGAAAATCA TCACTGTGGA GAAGCACCCA GATGCAGACA     780

GCCTGTATGT AGAGAAGATT GACGTGGGGG AAGCTGAACC ACGGACTGTG GTGAGCGGCC     840

TCGTACAGTT CGTGCCCAAG GAGGAACTGC AGGACAGGCT GGTAGTGGTG CTGTGCAACC     900
```

```
TGAAACCCCA GAAGATGAGA GGAGTCGAGT CCCAAGGCAT GCTTCTGTGT GCTTCTATAG     960

AAGGGATAAA CCGCCAGGTT GAACCTCTGG ACCCTCCGGC AGGCTCTGCT CCTGGTGAGC    1020

ACGTGTTTGT GAAGGGCTAT GAAAAGGGCC AACCAGATGA GGAGCTCAAG CCCAAGAAGA    1080

AAGTCTTCGA GAAGTTGCAG GCTGACTTCA AAATTTCTGA GGAGTGCATC GCACAGTGGA    1140

AGCAAACCAA CTTCATGACC AAGCTGGGCT CCATTTCCTG TAAATCGCTG AAAGGGGGA     1200

ACATTAGCTA GCCAGCCCAG CATCTTCCCC CCTTCTTCCA CCACTGAGTC ATCTGCTGTC    1260

TCTTCAGTCT GCTCCATCCA TCACCCATTT ACCCATCTCT CAGGACACGG AAGCAGCGGG    1320

TTTGGACTCT TTATTCGGTG CAGAACTCGG CAAGGGGCAG CTTACCCTCC CCAGAACCCA    1380

GGGATCATCC TGTCTGGCTG CAGTGAGAGA CCAACCCCTA ACAAGGGCTG GGCCACAGCA    1440

GGGAGTCCA                                                            1449
```

(2) INFORMATION FOR SEQ ID NO:3:

(i) SEQUENCE CHARACTERISTICS:
    (A) LENGTH: 310 amino acids
    (B) TYPE: amino acid
    (C) STRANDEDNESS: single
    (D) TOPOLOGY: linear (ii) MOLECULE TYPE: peptide (vii) IMMEDIATE SOURCE:
    (A) LIBRARY: GenBank
    (B) CLONE: 498910

(xi) SEQUENCE DESCRIPTION: SEQ ID NO:3:

```
Met Ala Thr Asn Asp Ala Val Leu Lys Arg Leu Glu Gln Lys Gly Ala
 1               5                  10                  15

Glu Ala Asp Gln Ile Ile Glu Tyr Leu Lys Gln Gln Val Ala Leu Leu
                20                  25                  30

Lys Glu Lys Ala Ile Leu Gln Ala Thr Met Arg Glu Glu Lys Lys Leu
            35                  40                  45

Arg Val Glu Asn Ala Lys Leu Lys Lys Glu Ile Glu Glu Leu Lys Gln
        50                  55                  60

Glu Leu Ile Leu Ala Glu Ile His Asn Gly Val Glu Gln Val Arg Val
 65                 70                  75                  80

Arg Leu Ser Thr Pro Leu Gln Thr Asn Cys Thr Ala Ser Glu Ser Val
                85                  90                  95

Val Gln Ser Pro Ser Val Ala Thr Thr Ala Ser Pro Ala Thr Lys Glu
                100                 105                 110

Gln Ile Lys Ala Gly Glu Glu Lys Val Lys Glu Lys Thr Glu Lys
            115                 120                 125

Lys Gly Glu Lys Lys Glu Lys Gln Gln Ser Ala Ala Ala Ser Thr Asp
    130                 135                 140

Ser Lys Pro Ile Asp Ala Ser Arg Leu Asp Leu Arg Ile Gly Cys Ile
145                 150                 155                 160

Val Thr Ala Lys Lys His Pro Asp Ala Asp Ser Leu Tyr Val Glu Glu
                165                 170                 175

Val Asp Val Gly Glu Ala Ala Pro Arg Thr Val Val Ser Gly Leu Val
            180                 185                 190

Asn His Val Pro Leu Glu Gln Met Gln Asn Arg Met Val Val Leu Leu
        195                 200                 205

Cys Asn Leu Lys Pro Ala Lys Met Arg Gly Val Leu Ser Gln Ala Met
    210                 215                 220
```

```
Val Met Cys Ala Ser Ser Pro Glu Lys Val Glu Ile Leu Ala Pro Pro
225                 230                 235                 240

Asn Gly Ser Val Pro Gly Asp Arg Ile Thr Phe Asp Ala Phe Pro Gly
            245                 250                 255

Glu Pro Asp Lys Glu Leu Asn Pro Lys Lys Ile Trp Glu Gln Ile
            260                 265                 270

Gln Pro Asp Leu His Thr Asn Ala Glu Cys Val Ala Thr Tyr Lys Gly
            275                 280                 285

Ala Pro Phe Glu Val Lys Gly Lys Gly Val Cys Arg Ala Gln Thr Met
    290                 295                 300

Ala Asn Ser Gly Ile Lys
305                 310
```

(2) INFORMATION FOR SEQ ID NO:4:

(i) SEQUENCE CHARACTERISTICS:
        (A) LENGTH: 388 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1184699

(xi) SEQUENCE DESCRIPTION: SEQ ID NO:4:

```
Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
```

-continued

```
225                 230                 235                 240
Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
                260                 265                 270

Ser Glu Phe Val Ile Leu Arg Asp Glu Lys Trp Gly Gly Asn Lys Thr
            275                 280                 285

Tyr Thr Ala Tyr Val Asp Leu Glu Lys Asp Phe Ala Ala Glu Val Val
        290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
                340                 345                 350

Gly Leu Pro Arg Ile Gln Asn Gln Arg Arg Ser Ser His Pro Gly Trp
            355                 360                 365

Ile Ser Val Trp Gly Lys Ser Ser Leu Trp Arg Ser Thr Gln Met Gln
        370                 375                 380

Thr Ala Cys Met
385
```